United States Patent [19]

Berlin et al.

[11] Patent Number: 4,581,361

[45] Date of Patent: Apr. 8, 1986

[54] 3-THIA-7-AZABICYCLO(3.3.L)NONANES AND DERIVATIVES AS ANTIARRHYTHMIC AGENTS

[75] Inventors: Kenneth D. Berlin, Stillwater; Benjamin J. Scherlag, Oklahoma City; Bruce R. Bailey, III, Indiahoma; Elizabeth M. Holt, Stillwater, all of Okla.

[73] Assignee: Oklahoma State University, Stillwater, Okla.

[21] Appl. No.: 397,453

[22] Filed: Jul. 12, 1982

[51] Int. Cl.$^4$ .................. A61K 31/435; A61K 31/38; C07D 471/02

[52] U.S. Cl. .................................... 514/301; 546/114

[58] Field of Search .......................... 546/114; 514/301

[56] References Cited

U.S. PATENT DOCUMENTS 4,127,580 11/1978 Braye .................................. 546/114

Primary Examiner—Henry R. Jiles
Assistant Examiner—Robert C. Whittenbaugh
Attorney, Agent, or Firm—Head, Johnson & Stevenson

[57] ABSTRACT

3-Thia-7-azabicyclo(3.3.1)nonanes and derivatives thereof are disclosed. The preparation of these compounds is given. Their use as antiarrhythmic agents is given.

29 Claims, No Drawings

3-THIA-7-AZABICYCLO(3.3.1)NONANES AND DERIVATIVES AS ANTIARRHYTHMIC AGENTS

BACKGROUND OF THE INVENTION

1. Field of the Invention

This invention relates to antiarrhythmic compositions. More specifically, the invention relates to certain 3-thia-7-azabicyclo[3.3.1]nonanes and derivatives thereof.

2. Description of the Prior Art 3-azabicyclo[3.3.1]nonanes, including bicyclic systems with one heteroatom such as N, S and O and various derivatives, are known and are documented in the chemical literature. In a recent Chemical Reviews article, 1981, Vol. 81, No. 2, pages 149–174, entitled "Chemistry of 3-Azabicyclo[3.3.1]nonanes" by R. Jeyaraman and S. Avila the synthesis, stereochemistry, and reactions of such compounds are reviewed. This article acknowledges the close resemblance of aza- and diazaadamantanes in conformation and stereochemistry to the 3-azabicyclo[3.3.1]nonanes as a cause for significant progress in the azabicyclononane (ABN) studies. The article further acknowledges the ease of formation of 3-ABNs from simple ketones and aldehydes through the Mannich reaction without the involvement of complicated reaction conditions and reagents and the ready availability of a reactive carbonyl group in most of the ABNs prepared as important reasons for widespread studies on ABNs.

According to the existing chemical literature, some derivatives of 3-ABN have been found to possess useful biological activities. The observed biological activities have included potent analgesic properties and antitusive activities as well as antagonism to analgesic effects and even weak narcotic antagonism depending on the particular compound involved. Some have displayed local anesthetic activity and simple 3-ABN is reportedly effective against influenza infection. Other derivatives of 3-ABN have displayed powerful ganglioplegic and hypotensive properties. Several have been found to be sedatives, antipyretics, and psycholaleptic and hypoglycemic agents. Some 3,7-diazabicyclo[3.3.1]nonanes possess antiarrhythmic potencies.

The Chemical Reviews article further described the subclass of 3-thia-7-azabicyclo[3.3.1]nonanes as being of much less interest and identifies a series of diphenyl and/or diaryl substituted derivatives as having been prepared through the Mannich reaction.

SUMMARY OF THE INVENTION

The present invention involves novel 3-thia-7-azabicyclo[3.3.1]nonanes compositions selected from the group consisting of:

(a)

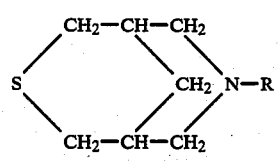

where R is

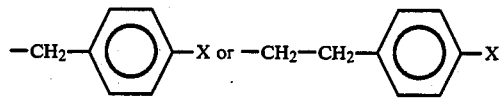

and X is either H, Cl or OCH$_3$;

(b)

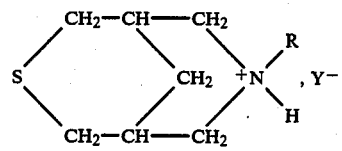

where R is

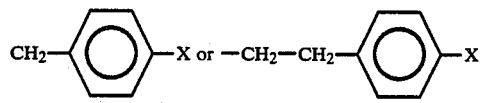

and X is either H, Cl or OCH$_3$ and Y is Cl, Br or ClO$_4$;

(c)

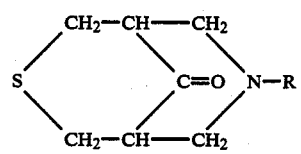

where R is

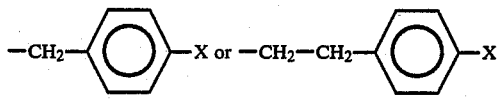

and X is either H, Cl or OCH$_3$;

(d)

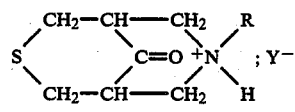

where R is

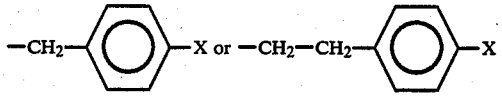

and X is either H, Cl or OCH$_3$ and Y is Cl, Br or ClO$_4$;

(e)

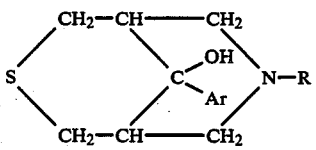

where R is

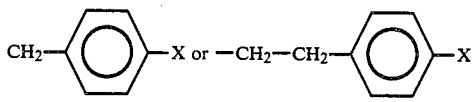

and X is either H, Cl, or OCH₃ and Ar is

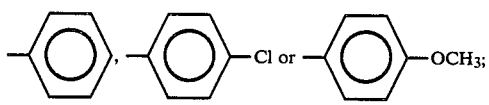

and (f)

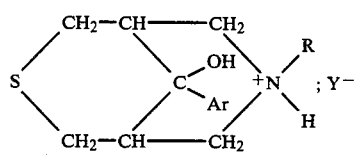

where R is

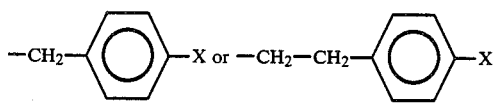

and X is either H, Cl or OCH₃ and Ar is

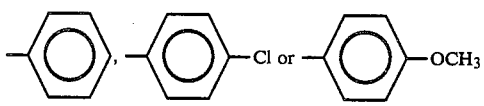

and Y is Cl, Br or ClO₄.

More specifically, the invention relates to 7-benzyl-3-thia-7-azabicyclo[3.3.1]nonane, its hydrogen perchlorate amine salt and the corresponding 9-hydroxyl-9-phenyl or 9-one derivatives. The present invention further provides for the use of the above compositions in an antiarrhythmic process.

Thus, it is an object of the present invention to provide novel compositions that display biological activity. Fulfillment of this object and the presence and fulfillment of other objects will be apparent upon complete reading of the specification and claims.

DESCRIPTION OF THE PREFERRED EMBODIMENTS

The chemical compositions according to the preferred embodiments of the present invention are heteronuclear ring organic compounds based on the 3-azabicyclo[3.3.1]nonane structure as follows:

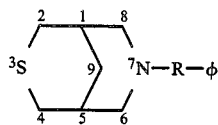

wherein the 3 position is a sulfur atom (thia) and the 7-position is an alkylated nitrogen atom (aryl substituted tertiary amine). The 9-position can either be an unsubstituted carbon, a carbonyl group or an arylated, hydroxylated carbon. The compounds with a carbonyl group at the 9-position will be referred to as bispidones and the others as bispidines.

These compounds are potential drugs for use in the treatment of disorders of the heart. They display good antiarrhythmic activity and as such are viable candidates to control arrhythmias in humans who have suffered major heart attacks or infarctions.

Typically, the ketones (e.g. bispidones) are synthesized by the reaction of tetrahydrothiopyranone with formaldehyde and benzylamine according to the Mannich reaction as follows:

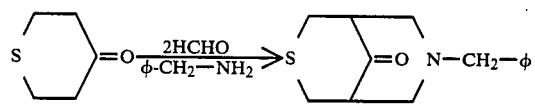

The corresponding bispidines and respective derivatives of either the bispidines and bispidones can be readily synthesized by making the appropriate selection of reactants for the Mannich reaction and/or by selective oxidation or reduction at the 9-position as exemplified later. The Mannich reaction is particularly useful in that, as previously indicated, it does not require complicated reaction conditions and reagents. However for purposes of the present invention, other methods of synthesis well known in the art should be considered equivalent. For example and for more detailed disclosure of various alternative methods of synthesis (including the Mannich reaction) and methods of synthesis of various subsequent derivatives, the previously mentioned Chemical Reviews article by Jeyaraman et al is again cited and herein incorporated by reference for such purposes. Furthermore, according to the preferred embodiments of the present invention, the water solubility of the 3-thia-7-azabicyclo[3.3.1]nonane compounds can be advantageously enhanced by formation of corresponding tertiary amines salts and the like prior to patient treatment.

In order to further illustrate the formation of the 3-thia-7-azabicyclo[3.3.1]nonane according to the present invention, the preparation and isolation of a purified, water soluble, biologically-active tertiary amine salt thereof and the antiarryhthmic activity of the compositions, the following sequence of examples are presented.

EXAMPLE I

Preparation of 7-Benzyl-3-thia-7-azabicyclo[3.3.1]nonan-9-one

A solution containing 0.46 g (4.3 mmol) of benzylamine and 1.0 g (33.0 mmol) of paraformaldehyde in 15 ml of methyl alcohol was made acidic with acetic acid (0.38 g). To this solution was added 0.5 g (4.3 mmol) or 4-thianone (tetrahydrothiopyranone), and the resulting solution was heated to reflux for 5-6 hours. Evaporation of the solvent on a rotary evaporator gave a heavy red oil which was partitioned between 30 ml of water and 30 ml of diethyl ether. The organic layer was discarded and the aqueous layer was made strongly basic with 0.3 g (7.5 mmol) of sodium hydroxide pellets. The resulting solution was extracted with diethyl ether (four 30 ml portions), and the extracts were combined and dried over Na₂SO₄. The dried solution (yellow) was filtered and evaporated on a rotary evaporator to give a brownish-yellow oil which solidified upon standing. Treatment of the solid with 100 ml of a petroleum ether sold under the tradename Skelly B (boiling point 60°–68° C.) on a steam bath for 30 minutes gave a solution which was filtered hot. Evaporation of the solvent produced 0.5 g of a light yellow solid. Sublimation (80°/0.025 mm) of this solid gave 0.4 g (38%) of the title compound melting at 91°–92° C.

Analytical confirmation of the structural formula:

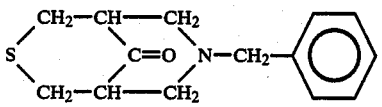

was as follows. Elemental analysis found 68.01% C; 6.96% H; 5.67% N and 13.07% S (by weight) which corresponds to the empirical formula $C_{14}H_{17}NOS$ (68.02 C, 6.88 H, 5.67 N and 12.95%S). Mass spectrometer peak matching of the molecular ion gave a mass to charge ratio of 247.1031 exactly corresponding to the theoretical m/e ratio. An absorption peak at 1720 cm$^{-1}$ was observed in the infrared spectra (KBr technique) corresponding to the presence of a carbonyl group. Both hydrogen and carbon-13 NMR spectral shifts were measured from the tetramethylsilane standard on a Varian XL(100) spectrometer confirming the correct hydrogen distribution and carbon atom spectral assignments as follows:

$^1$H NMR (DCCl$_3$) δ 2.25–3.25 [m, 10 H, ring H], 3.5 [s, 2 H, $\underline{CH_2}$Ar], 7.25 [m, 5 H, Ar-$\underline{H}$]and $^{13}$C NMR (DCCl$_3$) ppm: C(1,5) 47.06; C(2,4) 34.67; C(6,8) 58.30; C(9) 212.84; C$_6$H$_5$$\underline{CH_2}$ 61.30; C(Ar-$\underline{C}$) C(α) 137.93; C(β) 128.56; C (γ) 128.21; C(δ) 127.14.

EXAMPLE II

Preparation of 7-Benzyl-3-thia-7-azabicyclo[3.3.1]nonane Hydrogen Perchlorate To a solution of 10 ml of triethylene glycol which contained 2 g (62.5 mmol) of hydrazine was added 0.5 g (2.0 mmol) of 7-benzyl-3-thia-7-azabicyclo[3.3.1]nonan-9-one prepared according to the process of Example I. When the addition was complete, 3.5 g of potassium hydroxide pellets were added, and the resulting mixture was heated to 145°–150° C. under nitrogen for 4 hours. During this time, 1.5 ml of distillate was removed by the use of a fractional distillation take-off unit. After 4 hours, the solution which resulted was cooled to room temperature and then diluted with water (30 ml). This new solution was extracted with diethyl ether (three 30-ml portions). The ether extracts were combined and drived over MgSO$_4$. After the dried ether extracts were filtered, the resulting solution was cooled to 0° C. and 2 ml of perchloric acid (60% solution-Mallinckrodt, analytical Reagent) was slowly added. Small white needle-like crystals separated and were filtered and washed with fresh diethyl ether (50 ml). Recrystallization of the crystals was effected with 95% ethyl alcohol. The solid which resulted was placed in water (50 ml, room temperature) which contained 1.0 g of potassium hydroxide pellets. A suspension resulted which slowly became a solution upon stirring (5 minutes). Extraction of this solution followed with diethyl ether (three 30-ml portions), and the extracts were combined and dried over MgSO$_4$. Filtering removed the drying agent, and the resulting solution was cooled to 0° C. To this solution was slowly added a solution of 2 ml of perchloric acid 60%, same as above). Small white crystals separated and were filtered off and washed with fresh diethyl ether (50 ml). These crystals were dried for 20 minutes at room temperature/20 mm; the yield was 0.55 g (83%), m.p. 155°–156° C.

Analytical confirmation of the structural formula:

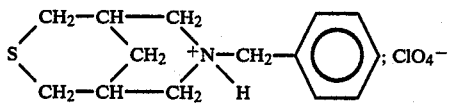

was as follows. Elemental analysis found 49.99% C; 6.07% H; 4.13% N; and 9.68% S (by weight) which corresponds to the empirical formula $C_{14}H_{20}ClNO_4S$ (50.37 C, 6.99 H, 4.19 N and 9.60%S). Mass spectrometer peak matching of the molecular ion gave a mass to charge ratio of 233.1228 compared to theoretical m/e of 233.1238. An absorption peak at 3400 cm$^{-1}$ was observed in the infrared spectra (KBr technique) corresponding to the presence of the nitrogen-hydrogen bond of the amine salt. Again, both hydrogen and carbon-13 NMR data was measured on a Varian XL(100) spectrometer using tetramethylsilane as the standard. The NMR results were as follows:

$^1$H NMR (DMSO-d$_6$) δ 1.6–3.1 [m, 12 H, ring H], 4.27 [s, 2 H, $\underline{CH_2}$-C$_6$H$_5$], 7.5 [m, 5 H, Ar-$\underline{H}$], 9.25 [s, 1 H, N$\underline{H}$] and $^{13}$C NMR [This data is for the free amine rather than for the perchlorate] (DCCl$_3$) ppm; C(1,5), 27.14; C(2,4) 31.49; C(6,8), 58.54; C(9) 29.76; C$_6$H$_5$$\underline{CH_2}$ 63.18; C(Ar-C) 126.35, 127.84, 128.37, 138.96.

EXAMPLE III

Preparation of 9-Hydroxyl-9-phenyl-7-benzyl-3-thia-7-azabicyclo[3.3.1]nonane Hydrogen Perchlorate A solution of 0.95 g (6.1 mmol) of bromobenzene in 40 ml of dry diethyl ether was slowly added over a period of one hour to 0.2 g (8.3 g. at.) of magnesium in a round bottom flask equipped with a magnetic stirrer. This mixture was allowed to stir for one hour under nitrogen. The Grignard reagent formed was then treated with 0.5 g (2.0 mmol) of 7-benzyl-3-thia-7-azabicyclo[3.3.1]nonan-9-one which was dissolved in 25 ml of ether. The addition was performed slowly and stirring was continued for one hour.

After this time, 20 ml of 9M H$_2$SO$_4$ was added slowly, and the resulting mixture was stirred for one hour. Two layers separated and the ether layer was discarded. After cooling the organic layer in an ice bath, the layer was made basic with KOH pellets. This basic mixture was diluted with 100 ml of water and was then extracted with 3–20 ml portions of ether which were combined and dried (KOH). The ether solution was decanted into a dry beaker. To this solution was added dropwise a solution of perchloric acid (60% in water) with stirring until no additional white percipitate formed. The white solid observed was filtered and washed with 20 ml of fresh ether. Recrystallization (95% ethanol) of the white solid gave 0.69 g (81%) of the title alcohol, melting at 249°–250° C.

Analytical confirmation of the structure was as follows. Elemental analysis found 56.45% C; 5.70% H; 3.27% N; 7.65% S; and 8.70% Cl (by weight) which corresponds to the empirical formula $C_{20}H_{24}NO_5SCl$ (56.40 C, 5.64 H, 3.29 N, 7.52 S and 8.34% Cl). An absorption peak occurred at 3490 cm$^{-1}$ in the infrared spectrum of the title compound.

Since the salt was not soluble in all of the common solvents examined and often used for NMR analysis, the material was converted to the free amine. The salt was placed in water and the solution was made basic (NaOH). Extraction of this solution was achieved with 3 50-ml portions of diethyl ether. The extracts were combined and dried (Na$_2$SO$_4$). Evaporation of the ether gave the solid aminoalcohol, 9-hydroxyl-9-phenyl-7-benzyl-3-thia-7-azabicyclo[3.3.1]nonane which melted at 112°–113° C. NMR spectral data on this free amine are as follows. $^1$H NMR (DCCl$_3$) δ 2.2[s, 1 H, OH], 2.4–3.0 [m, 8 H], 3.65–3.75 [dd, 2 H], 3.3 [s, 2 H, Ar-CH$_2$], and 7.15–7.4 [m, 10 H, Ar-H].

EXAMPLE IV

Using four dogs and three dosage rates (i.e., 6, 12 and 18 mg/kg; i.e., mg of compound per kg of body weight of dog) of the hydrogen perchlorate salt prepared according to Example II dissolved in 50% ethanol, the following techniques were employed and respective results were obtained.

In the anesthetized dog (30 mg/kg-sodium pentobarbital administered intravenously), the left anterior descending coronary artery was ligated and the animal allowed to recover for 24 hours. Under anesthesia and controlled ventilation, a 12-lead electrocardiogram was taken to establish the presence of transmural myocardial infarction. At this time ventricular escape beats and multifocal accelerated idioventricular rhythms were commonly seen interspersed with the sinus rhythm.

The original left-lateral thoracotomy was reopened and the following electrical recordings were made: standard leads II of the electrocardiogram; His bundle electrogram via a catheter in the left ventricle in contact with the infarcted endocardium bordering the infarct; an electrode catheter in the right ventricle in contact with non-infarcted endocardium; a special composite electrode on the left ventricular epicardial surface overlying the infarct; another composite electrode on the non-infarcted posterior epicardium of the left ventricle. Mean arterial blood pressure was monitored continuously. Two silver wires were inserted into the left vagosympathetic trunk. By delivering high frequency (20 Hz) square wave pulses to the nerve trunk, the heart rate could be slowed sufficiently to expose the underlying ventricular rhythm. In this way the ventricular automaticity could be unmasked without interference of a competing sinus pacemaker. Other pairs of wires were inserted into the right artium for artrial pacing and the right ventricle for ventricular pacing.

Vagal stimulation was applied to determine the underlying ventricular automatically, which, in these preparations, averaged≃164/min. Atrial pacing at rates from 180/min up to the rate at which second degree A-V block was induced (≃300/min) was performed before and after drug administration in order to determine the effects of the compound upon intraatrial, A-V nodal, His-Purkinje, and ventricular muscle conduction. Ventricular pacing was then instituted by randomly introducing three ventricular paced beats at rates from 240 to 420/min. It was found that this method results in the induction of rapid sustained ventricular tachycardia (averaging 350/min). If rapid pacing or cardioversion is not instituted within one to two minutes, these tachycardias degenerate into ventricular fibrillation. Furthermore, the recording of continuous electrical activity (during the tachycardia), usually from the epicardial area overlying the infarct, suggests a reentrant rather than an automatic mechanism for this arrhythmia.

Four dogs were studied with the 3-thia-7-ABN composition of Example II. In the control state, two types of arrhythmias were seen. There were spontaneous and intermittent accelerated idoventricular rhythms whose rate averaged 164/min. Also, sustained rapid ventricular tachycardias could be induced by ventricular paced beats. These tachycardias, which were consistently monomorphic (QRS complex), averaged 340/min. The compound caused little or no change in the spontaneous arrhythmias (which were due to an automatic mechanism), but markedly slowed the induced tachycardia (due to a reentrant mechanism) by as much as 100 beats/min. In some cases after addition of the drug, the tachycardias were either not inducible or self-terminating. The peak effects occurred at doses of 6–12 mg/kg. No further response was noted at 18 mg/kg. The duration of action was 20–40 minutes. In one case, before addition of the drug, ventricular fibrillation was induced rather than created via ventricular tachycardia by ventricular pacing. This induction occurred at the low rate of 240 beats/min. Indeed the compound caused the induction of ventricular fibrillation as a result of ventricular pacing but at the rate of 360–390/min. Forty minutes after the drug effect had subsided, the ventricular fibrillation was again induced at a rate of 240/min. Insofar as the effect of the compound on conduction, there was little or no effect on intraatrial, His-Purinkje and ventricular muscle conduction. A-V nodal conduction was slightly enhanced at all doses.

In addition, the compound causes a 10–15% increase in mean blood pressure during sinus rhythm and during sustained ventricular tachycardia. In the control states, blood pressure was so low during sustained ventricular tachycardia (≃20 mmHg) that cardioversion or electrical pacing had to be used to terminate the arrhythmia. Such termination prevented degeneration of the sustained ventricular tachycardia into ventricular fibrillation. After the addition of the drug, mean arterial blood pressure was 50–60% higher, and, moreover, the tachycardia was slower. Therefore, the arrhythmia was easily tolerated for long periods without degeneration into ventricular fibrillation. No change in the effects of vagal stimulation were seen with this agent, that is, the degree of sinus inhibition and/or A-V block were similar before and after the drug.

Thus use of 7-benzyl-3-thia-7-azabicyclo[3.3.1]nonane hydrogen perchlorate and related compounds is viewed as promising in that induced ventricular tachycardias, which are life-threatening can be markedly slowed and most important, blood pressure, instead of being depressed, is actually increased so that the malignant character of the ventricular arrhythmia, i.e., production of symptoms, is dramatically removed. In the context of use of such an agent, the goal of therapy would be to abolish symptoms, i.e., lightheadness, syncope, and in this way prevent sudden death. Thus, the use of high doses of depressant substances would not be necessary to prevent absolute inducibility of ventricular arrhythmias and their commonly associated fatal consequences.

Fifty percent ethanol solution was injected into the dogs in order to determine if some or any of the effects of the drug were due to the solvent. Ethanol injected intravenously in appropriate volumes produced a small but transient decrease in arterial blood pressure and no appreciable changes into ventricular ectopic activity either of the automatic or the reentrant type. There were no other remarkable responses to ethanol injections.

Since recent* reports have indicated that calcium blockers, such as verapamil and nifedipine, have antiarrhythmic properties, several experiments were performed to examine the comparative calcium blocking properties. Comparison of the effects of the composition of Example II versus those of verapamil or D-600 drugs on the electrophysiology and hemodynamics of the 24-hour infarcted dog heart is summarized in the following table of results:

TABLE

|  | 7-Benzyl-3-thia-7-azabicyclo[3.3.1]nonane Hydrogen Perchlorate Solution | Known Calcium Blockers |
| --- | --- | --- |
| Sinus rate | No Change | Decrease |
| A-V conduction time | Decrease | Increase |
| Accelerated idioventricular rate | No change | Decrease |
| Sustained ventricular tachycardia | Decrease | No Change |
| Blood pressure | Increase | Decrease |

Thus, the above evidence suggests that compositions of the present invention have several actions which are diametrically opposite to those of known calcium blocking agents and that 7-benzyl-3-thia-7-ABN hydrogen perchlorate does not appear to be a calcium blocker.

EXAMPLE V

Studies on the Comparison of Examples I, II and III in Subacute Stages of Myocardial Infarctions in Dogs The studies which are outlined use the compositions produced in EXAMPLES I, II and III as well as the clinically-used drug lidocaine for comparison purposes in the treatment of induced ventricular tachycardias of infarcted dog heart 4 days after the left anterior artery occlusion. Electrodes were positioned on the heart for examination of the electrogram behavior in areas of slow conduction which are critical to the initiation and maintenance of arrhythmias. For this purpose, the 4-day infarcted heart was pretreated with methylprednisolone. The first electrical recordings were made from an infarcted dog heart 4 days after the left anterior coronary artery was occluded. It was observed that the area over the infarct was viable but sick since the electrogram displayed a low amplitude and was intermittently fractionated. The first four beats showed a 2:1 pattern of fractionation in the (IZ eg) recording. The next three beats showed a progressive delay of the fractionation in a Wenckebach fashion until a portion of the fractionated potential occurred after the T wave of the previous sinus beat. This is coincident with the occurrence of a premature ventricular beat (VPB). The sequence of events suggested a reentrant mechanism whereby conduction delay of the impulse in the infarcted zone was sustained, compared to the refractoriness of the rest of the heart, and reentered the normal tissues causing an ectopic beat. The mean blood pressure recorded during this sequence was 103 mm Hg.

When lidocaine (3 mg/kg), the standard antiarrhythmic agent, was used, a dramatic effect on the reentrant arrhythmia was observed as expected. The IZ eg recording was diminished in amplitude and displayed a 2:1 pattern with a fractionated potential in one beat alternating with one component in the next beat. This is associated with a suppression of the ventricular ectopic beats since the fractionated potential in every other beat did not extend beyond the T wave to induce a reentrant ectopic beat. However, in the third beat a ventricular ectopic beat manifested as a fusion beat F (there was observed a short P-R interval and aberrant QRS complex). This is associated with a fractionated potential, well beyond the previous T wave allowing a reentrant activation to occur. Mean blood pressure was slightly depressed by lidocaine and was in the range 103–95 mm Hg.

With a higher dose of lidocaine (6 mg/kg), there was observed a further depression of the electrogram amplitude (IZ eg) and the 2:1 pattern of the morphology of the electrogram was evident from beat to beat. There was complete suppression of the ventricular ectopic beats and the mean blood pressure stabilized at 95 mm Hg.

After a period of twenty minutes, the effect of the larger dose of lidocaine had dissipated. There was observed a return of the electrogram pattern of Wenckebach which is normally associated with a ventricular ectopic beat (VPB) after two sinus beats. The mean blood pressure returned to control levels, namely 106 mm Hg.

A dose of the composition of EXAMPLE II (3 mg/kg) was given intravenously in a solution of 1:1 water:ethanol with a total volume of 3.3 ml. Within one minute, the blood pressure rose from 106 to 138 mm HG. At the same time there was observed a marked depression of the amplitude of the IZ eg potentials and a 2:1 alternation of the configuration of the recorded deflections. Moreover, there was a sharp fractionation of the IZ eg potentials indicating that EXAMPLE II markedly slowed the conduction in the abnormal tissue. Potentials in the other areas observed were relatively unaffected. In contrast to the action of lidocaine at the same dose level, EXAMPLE II showed a more potent antiarrhythmic effect related to its selective depression of the conduction in the reentrant pathway depressed tissue). Quite significant was the observation that rather than depressing blood pressure, EXAMPLE II caused a substantial pressor effect (28%).

After a period of 40 minutes, the effect of EXAMPLE II had ceased as evidenced by a return of the electrical and hemodynamic properties to the control state. Addition of the composition of EXAMPLE I (3 mg/kg) caused a smaller change in electrical properties compared to that observed with EXAMPLE II. The amplitude of the potentials recorded from the IZ eg were not as diminished, and, although the 2:1 pattern of block was produced in relation to the fractioned potential, the deflection showed progressive fragmentation and delay which occasionally manifested as a ventricular ectopic beat (VPB). In this beat, the delayed potential occurred after the end of the T wave of the previous sinus beat. Mean blood pressure was elevated from 108 to 124 mm Hg.

Again after the effect of EXAMPLE I had ceased, a solution of the composition of EXAMPLE III was injected (3 mg/kg). The effects of the marked depression of the IZ eg electrograms and the disappearance of the arrhythmias appeared similar to those observed with EXAMPLE II. There was also a widening of the QRS duration (from 45-75 msec) and H-V interval (from 32-45 msec). Also, the endocardial electrogram was diminished slightly and delay occurred between the Purkinje potential (p) and muscle potential (M). Thus, it appears that this EXAMPLE III is less sensitive in terms of its negative dromotropic action since both normal and abnormal tissues are affected. In a few cases with EXAMPLE II at high doses (18 mg/kg), a similar widening of the QRS complex was noted and caused ventricular ectopic bears. Mean blood pressure with EXAMPLE III was still elevated (from 108 to 120 mm Hg).

In summary, there is good evidence that EXAMPLE II has a more potent effect on arrhythmias due to conduction defects in ischemically damaged hearts than does the clinically-used lidocaine at similar doses. In addition, a positive pressor response is associated with EXAMPLE II but not with lidocaine. The relative, namely EXAMPLE I, had less effect on the abnormal conduction but did show a positive blood pressure effect. EXAMPLE III raised blood pressure slightly but also had a potent depressant effect on normal and abnormal areas of conduction. Consequently, there appears to be a profile of useful activity in this particular family of heterocycles.

In principle, it is felt that the compositions of the present invention can be employed by themselves, in combination with each other, or in combination with other drugs to achieve either individually or in combination the desired antiarrhythmic properties. It is envisioned that the composition can be utilized and administered in a variety of methods including by way of example, but not limited thereto, intravenously, orally, suppository, inhalation, and the like. Furthermore, it is generally felt that the compositions as claimed either specifically possess antiarrhythmic activity or generally are broadly biologically active or the respective compositions are intermediaries to antiarrhythmic and biologically active species that are released or created in situ as the result of the administration of the drug.

Having thus described and exemplified the preferred embodiments with a certain degree of particularity, it is to be understood that the invention is not to be limited to the embodiments set forth herein for purposes of exemplification, but is to be limited only by the scope of the attached claims, including a full range of equivalents to which each element thereof is entitled.

We claim:

1. An antiarrhythmic compound selected from the group consisting of:

(a)

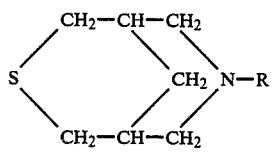

where R is

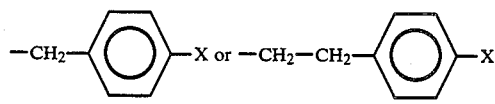

and X is either H, Cl or OCH$_3$;

(b)

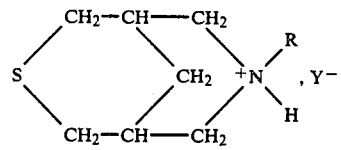

where R is

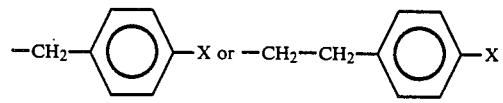

and X is either H, Cl, or OCH$_3$ and Y is Cl, Br, or ClO$_4$;

(c)

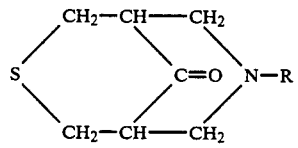

where R is

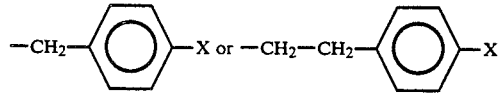

and X is either H, Cl or OCH$_3$;

(d)

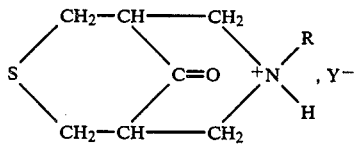

where R is

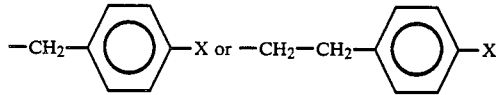

and X is either H, Cl or OCH$_3$ and Y is Cl, Br, or ClO$_4$;

(e)

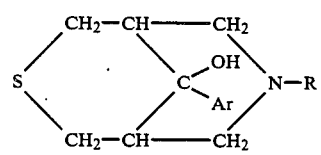

where R is

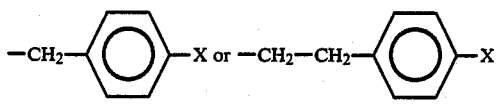

and X is either H. Cl or OCH₃ and Ar is

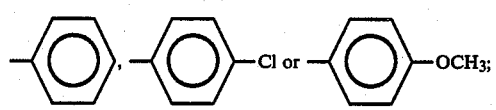

(f)

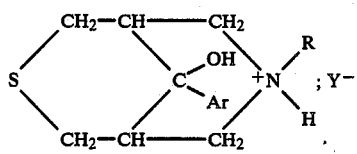

where R is

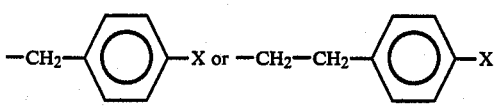

and X is either H. Cl or OCH₃ and Ar is

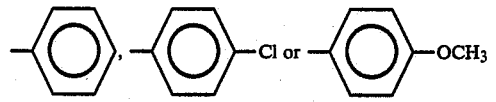

and Y is Cl, Br or ClO₄.

2. An antiarrhythmic compound of claim 1 having the formula:

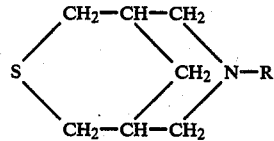

where R is

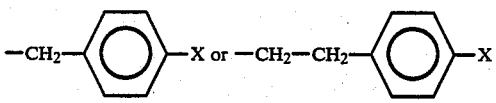

and X is either H, Cl or OCH₃.

3. An antiarrhythmic compound of claim 1 having the formula:

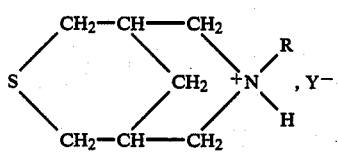

where R is

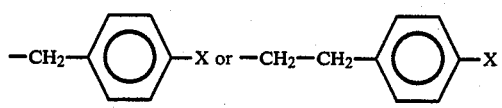

and X is either H, Cl or OCH₃ and Y is Cl, Br, or ClO₄.

4. An antiarrhythmic compound of claim 1 having the formula:

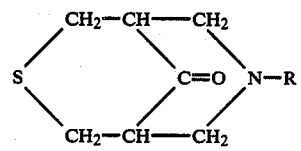

where R is

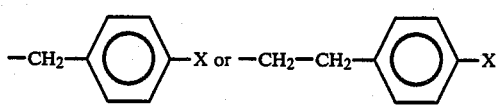

and X is either H, Cl or OHC₃.

5. An antiarrhythmic compound of claim 1 having the formula:

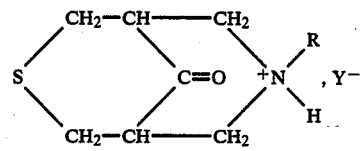

where R is

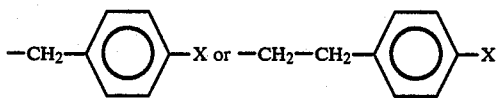

and X is either H, Cl, or OCH₃ and Y is Cl, Br, or ClO₄.

6. An antiarrhythmic compound of claim 1 having the formula:

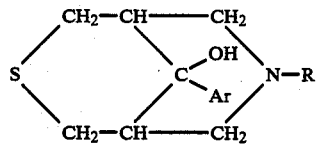

where R is

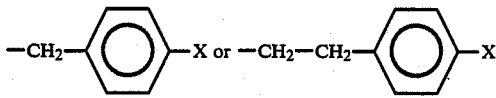

and X is either H, Cl or OCH₃ and Ar is

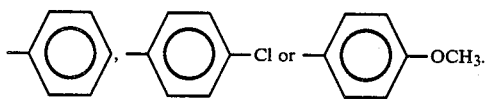

7. An antiarrhythmic compound of claim 1 having the formula:

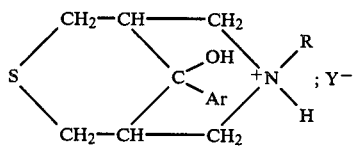

where R is

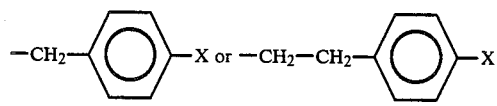

and X is either H, Cl or OCH₃ and Ar is

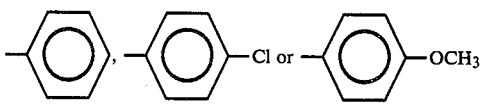

and Y is Cl, Br or ClO₄.

8. An antiarrhythmic compound of claim 2, 4 or 6 wherein R is

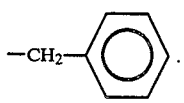

9. An antiarrhythmic compound of claim 3, 5 or 7 wherein R is

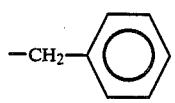

and Y is ClO₄.

10. An antiarrhythmic process comprising the step of administering a dosage an antiarrhythmically effective amount of a compound selected from the group consisting of:

(a)

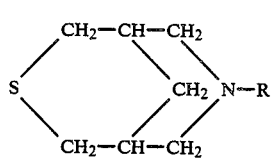

where R is

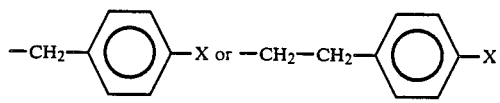

and X is either H, Cl, or OCH₃;

(b)

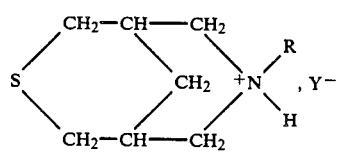

where R is

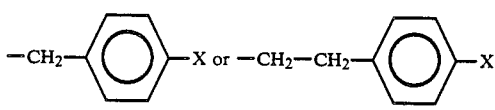

and X is either H, Cl, or OCH₃ and Y is Cl, Br, or ClO₄;

(c)

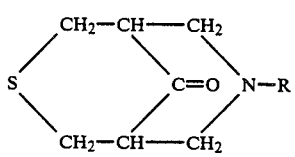

where R is

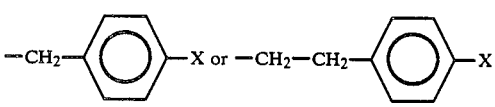

and X is either H, Cl, or OCH₃;

(d)

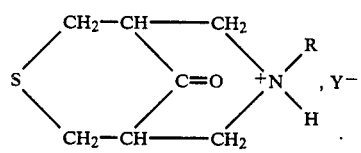

where R is

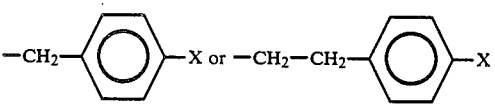

and X is either H, Cl or OCH₃ and Y is Cl, Br, or ClO₄;

(e)

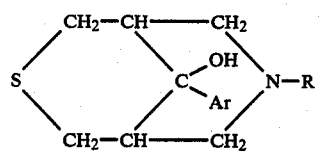

where R is

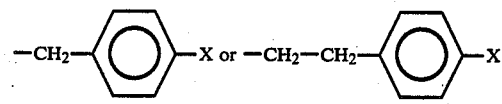

and X is either H, Cl or OCH₃ and Ar is

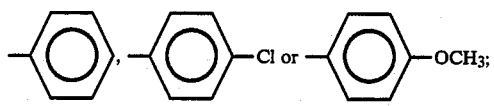

and
(f)

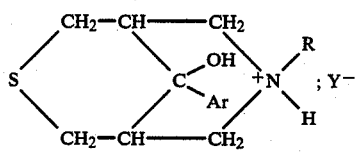

where R is

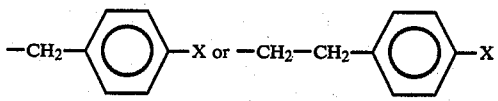

and X is either H, Cl or OCH₃ and Ar is

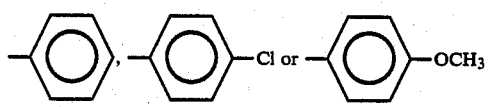

and Y is Cl, Br or ClO₄.

11. An antiarrhythmic process of claim 10 wherein the compound has the formula:

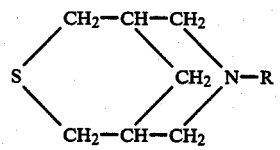

where R is

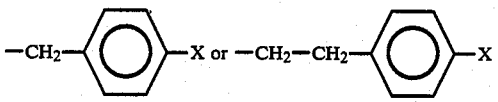

and X is either H, Cl or OCH₃.

12. An antiarrhythmic process of claim 10 wherein the compound has the formula:

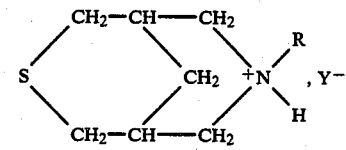

where R is

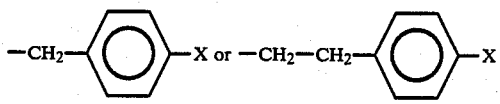

and X is either H, Cl or OCH₃ and Y is Cl, Br, or ClO₄.

13. An antiarrhythmic process of claim 10 wherein the compound has the formula:

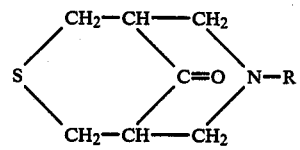

where R is

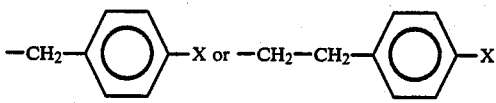

and X is either H, Cl or OCH₃.

14. An antiarrhythmic process of claim 10 wherein the compound has the formula:

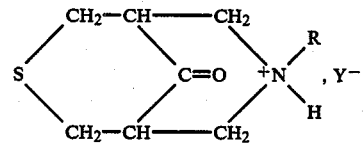

where R is

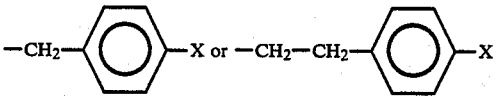

and X is either H, Cl or OCH₃ and Y is Cl, Br, or ClO₄.

15. An antiarrhythmic process of claim 10 wherein the compound has the formula:

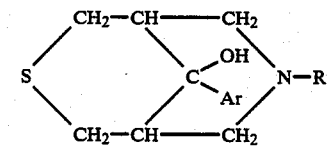

where R is

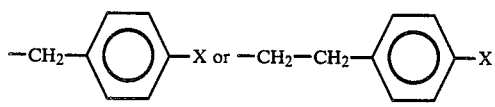

and X is either H, Cl or OCH₃ and Ar is

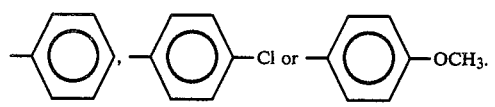

16. An antiarrhythmic process of claim 10 wherein the compound has the formula:

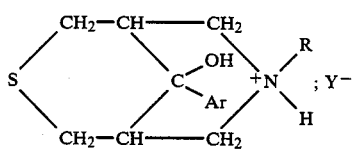

where R is

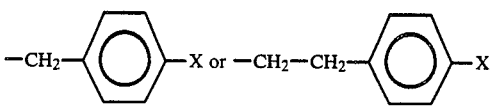

and X is either H, Cl or OCH₃ and Ar is

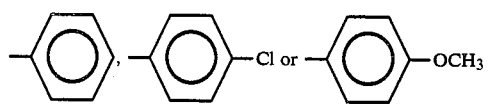

and Y is Cl, Br and ClO₄.

17. An antiarrhythmic process of claim 12 wherein said compound is 7-Benzyl-3-thia-7-azabicyclo[3.3.1-]nonane hydrogen perchlorate.

18. An antiarrhythmic process of claim 17 wherein said doage rate is from about 6 mg/kg to about 18 mg/kg.

19. A 3-thia-7-azabicyclo[3.3.1]nonane compound selected from the group consisting of:

(a)

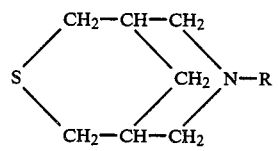

where R is

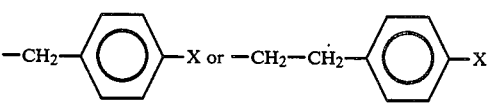

and X is either H, Cl or OCH₃;

(b)

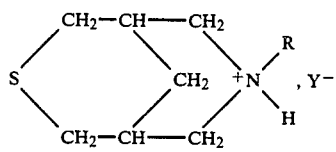

where R is

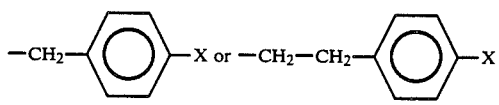

and X is either H, Cl or OCH₃ and Y is Cl, Br, or ClO₄;

(c)

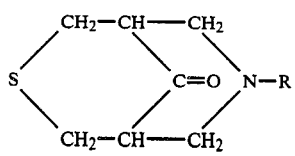

where R is

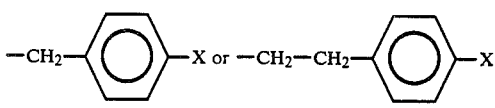

and X is either H, Cl or OCH₃;

(d)

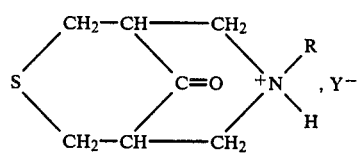

where R is

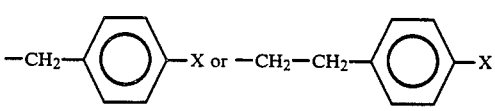

and X is either H, Cl or OCH₃ and Y is Cl, Br, or ClO₄;

(e)

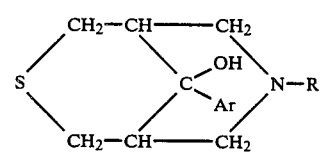

where R is

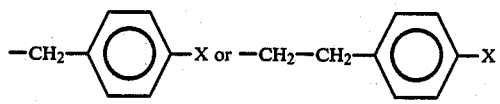

and X is either H, Cl or OCH₃ and Ar is

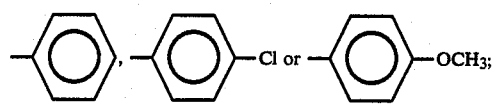

and
(f)

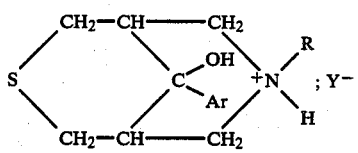

where R is

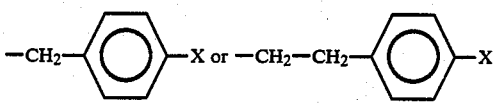

and X is either H, Cl or OCH₃ and Ar is

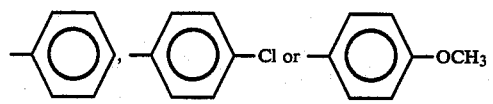

and Y is Cl, Br, or ClO₄.

20. A compound of the formula:

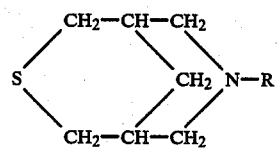

where R is

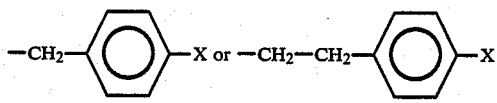

and X is either H, Cl or OCH₃.

21. A compound of the formula:

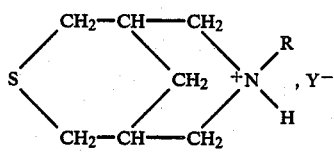

where R is

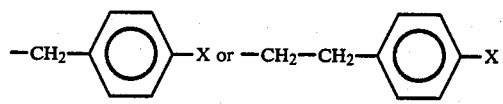

and X is either H, Cl or OCH₃ and Y is Cl, Br, or ClO₄.

22. A compound of the formula:

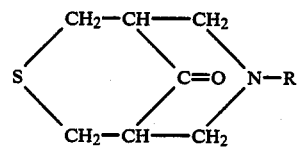

where R is

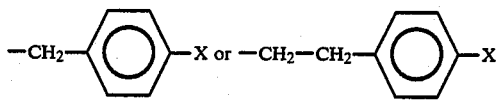

and X is either H, Cl or OCH₃.

23. A compound of the formula:

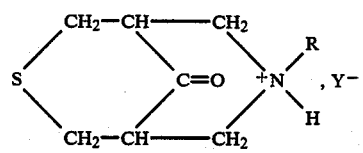

where R is

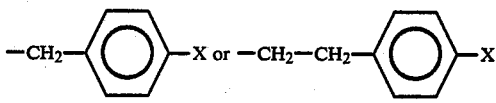

and X is either H, Cl or OCH₃ and Y is Cl, Br, or ClO₄.

24. A compound of the formula:

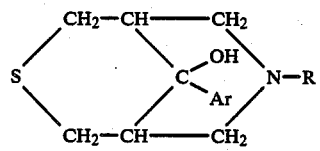

where R is

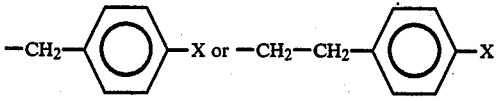

and X is either H, Cl or OCH₃ and Ar is

25. A compound of the formula:

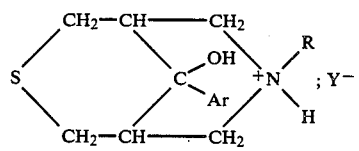
where R is
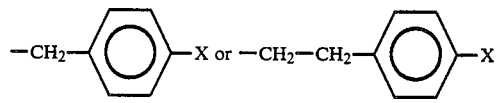
and X is either H, Cl or OCH₃ and Ar is
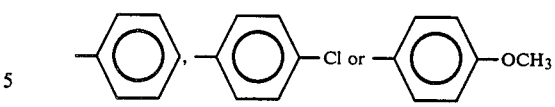
and Y is Cl, Br or ClO₄.
26. The compound 7-benzyl-3-thia-7-azabicyclo[3.3.1]nonan-9-one.
27. The compound 7-benzyl-3-thia-7-azabicyclo[3.3.1]nonane.
28. The compound 9-hydroxyl-9-phenyl-7-benzyl-3-thia-7-azabicyclo[3.3.1]nonane.
29. The amine acid salt of the compound of claims 23, 24 or 25 wherein said acid is selected from the group consisting of HCl, HBr, and HClO₄.
* * * * *